(12) United States Patent
Torres et al.

(10) Patent No.: US 10,188,395 B2
(45) Date of Patent: Jan. 29, 2019

(54) NON-PLANAR HEATING CHAMBER DETACHMENT MECHANISM OF AN IMPLANTABLE VASO-OCCLUDING DEVICE DELIVERY SYSTEM

(71) Applicant: DePuy Synthes Products, LLC, Raynham, MA (US)

(72) Inventors: Michael Torres, Tracy, CA (US); Eugene Young, Union City, CA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 517 days.

(21) Appl. No.: 14/971,474

(22) Filed: Dec. 16, 2015

(65) Prior Publication Data

US 2017/0172579 A1    Jun. 22, 2017

(51) Int. Cl.
*A61M 29/00* (2006.01)
*A61B 17/12* (2006.01)
*A61B 17/00* (2006.01)

(52) U.S. Cl.
CPC .... *A61B 17/12022* (2013.01); *A61B 17/1214* (2013.01); *A61B 17/12109* (2013.01); *A61B 2017/00411* (2013.01); *A61B 2017/00526* (2013.01); *A61B 2017/12068* (2013.01)

(58) Field of Classification Search
CPC ........ A61B 17/12022; A61B 17/12109; A61B 17/12113; A61B 17/12118; A61B 17/1214; A61B 17/12145; A61B 17/1215; A61B 17/12154; A61B 2017/1205; A61B 2017/12054; A61B 2017/12068; A61B 2017/12072; A61B 2017/12077
USPC ....................................................... 606/191
See application file for complete search history.

(56) References Cited

U.S. PATENT DOCUMENTS

| 5,108,407 | A | 4/1992 | Geremia et al. |
|---|---|---|---|
| 5,989,242 | A | 11/1999 | Saadat et al. |
| 6,059,815 | A | 5/2000 | Lee et al. |
| 6,102,917 | A | 8/2000 | Maitland et al. |
| 7,591,833 | B2 | 9/2009 | Jones et al. |
| 7,789,891 | B2 | 9/2010 | Wallace |
| 8,226,680 | B2 | 7/2012 | Wallace |
| 2010/0160903 | A1 | 6/2010 | Krespi |

(Continued)

FOREIGN PATENT DOCUMENTS

| BR | 1020 1300 7869 | 6/2015 |
|---|---|---|
| CA | 2 492 452 | 1/2004 |

(Continued)

OTHER PUBLICATIONS

European Search Report in counterpart application (EP16204280.8-1664) dated Apr. 25, 2017 (9 pages).

*Primary Examiner* — Melanie R Tyson
(74) *Attorney, Agent, or Firm* — Cohen & Hildebrand, PLLC

(57) ABSTRACT

A delivery system for an implantable vaso-occluding device. A non-planar heating chamber is disposed proximate to a distal end of an advancing member. Protruding from an interior surface of the non-planar heating chamber is a detachment fiber made from a polymeric material and having a closed distal end. At least one heating element is disposed on the interior surface of the non-planar heating chamber to produce sufficient heat to sever the detachment fiber. An articulation point is established between the vaso-occluding device and the delivery system. The vaso-occluding device remains at all times substantially self-centered while being advanced.

14 Claims, 3 Drawing Sheets

(56) References Cited

U.S. PATENT DOCUMENTS

2010/0160944 A1 6/2010 Teoh
2013/0261659 A1 10/2013 Lorenzo
2014/0277093 A1 9/2014 Guo et al.

FOREIGN PATENT DOCUMENTS

WO 01/58366 8/2001
WO 2015/026576 2/2015

NON-PLANAR HEATING CHAMBER DETACHMENT MECHANISM OF AN IMPLANTABLE VASO-OCCLUDING DEVICE DELIVERY SYSTEM

BACKGROUND OF THE INVENTION

Field of the Invention

The present invention is directed to a delivery system for an implantable vaso-occluding device. In particular, the present invention relates to a non-planar heating chamber detachment mechanism using heat energy to release a detachment fiber securing the delivery system to the vaso-occluding device.

Description of Related Art

Embolization is a nonsurgical, minimally invasive procedure that selectively occludes (e.g., deliberately blocks) a blood vessel by purposely introducing an occluding device (e.g., an embolic coil) into the blood vessel. It is now commonplace to use catheter delivery systems for positioning and deploying such occluding devices, such as dilation balloons, stents and embolic coils, in the vasculature of the human body for treating endovascular diseases such as blocked arteries and aneurysms. Occluding devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat defects of intracranial blood vessels.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the occlusion device through the catheter and out of the distal end of the catheter at a desired delivery site. Some of the problems that have been associated with these procedures relate to the accuracy of occlusion device placement. For example, the force employed to eject the occlusion device from the delivery catheter may cause the occlusion device to over shoot the predetermined site or dislodge previously deployed occlusion devices. Also, once the occlusion device is pushed out of the distal end of the catheter, the occlusion device cannot be retracted and may migrate to an undesired location. Often, retrieving and repositioning the occlusion device requires a separate procedure and has the potential to expose the patient to additional risk.

Once properly navigated through the vasculature of the patient to the target treatment site, the embolic coil is detached from its delivery system. Conventional forms of detachment have been used to sever the occluding device from its delivery system. Several known methods of detachment include electrical heating, mechanical interference or hydraulic and electrolytic detachment. Each of these conventional detachment mechanisms suffer from one or more disadvantages such as large stiff regions, inconsistent detachment of the occlusion device from its delivery system and/or extended detachment duration.

It is therefore desirable to develop an improved electrical heating detachment system and method for a vascular occluding device.

SUMMARY OF THE INVENTION

An aspect of the present invention relates to an improved electrically heated detachment system for an implantable vaso-occluding device that is reduced in size so that it may be used in the brain or other small target sites of the body to be treated.

While another aspect of the present invention is directed to an improved electrically heated detachment mechanism for an occluding device including a non-planar chamber for heating and releasing the detachment fiber.

Still a further aspect of the present invention is directed to a delivery system for an implantable vaso-occluding device, wherein the delivery system includes an advancing member having a distal end and an opposite proximal end. A non planar heating chamber is disposed proximate to the distal end of the advancing member, wherein the non-planar heating chamber has an interior surface facing away from the distal end of the advancing member and an opposite exterior surface facing the distal end of the advancing member. Protruding from the interior surface of the non-planar heating chamber is a detachment fiber made from a polymeric material and having a closed distal end. At least one heating element is disposed on the interior surface of the non-planar heating chamber to produce heat for releasing the detachment fiber.

Another aspect of the present invention is directed to a method for assembling a delivery system for an implantable vaso-occluding device as described in the preceding paragraph. The at least one heating element is positioned on the interior surface of the non-planar heating chamber. Then exterior surface of the non-planar heating chamber is secured to the distal end of the advancing member. One of two terminating free ends of the detachment fiber is threaded through a securing member disposed on the vaso-occluding device until the securing member reaches the closed distal end of the detachment fiber. The two terminating free ends of the detachment fiber along with the vaso-occluding device are secured to the distal end of the advancing member with the non-planar heating chamber disposed therebetween. The at least one heating element disposed on the interior surface of the non-planar heating chamber produces heat for releasing the detachment fiber.

While yet another aspect of the present invention relates to a method for positioning an implantable vaso-occluding device at a target site within a blood vessel using a delivery system as previously described above. Using a delivery catheter, the delivery system is introduced into the blood vessel. The delivery catheter is then advanced through the blood vessel to the target site. Once at the target site in the blood vessel, the advancing member is deployed to project the vaso-occluding device from the delivery catheter. The at least one heating element is energized by a power source to produce heat energy sufficient to sever the detachment fiber thereby freeing the vaso-occlusive device at the target site in the blood vessel. Lastly, the delivery catheter and the advancing member disposed therein are extracted from the blood vessel while maintaining the vaso-occlusive device located at the target site in the blood vessel.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
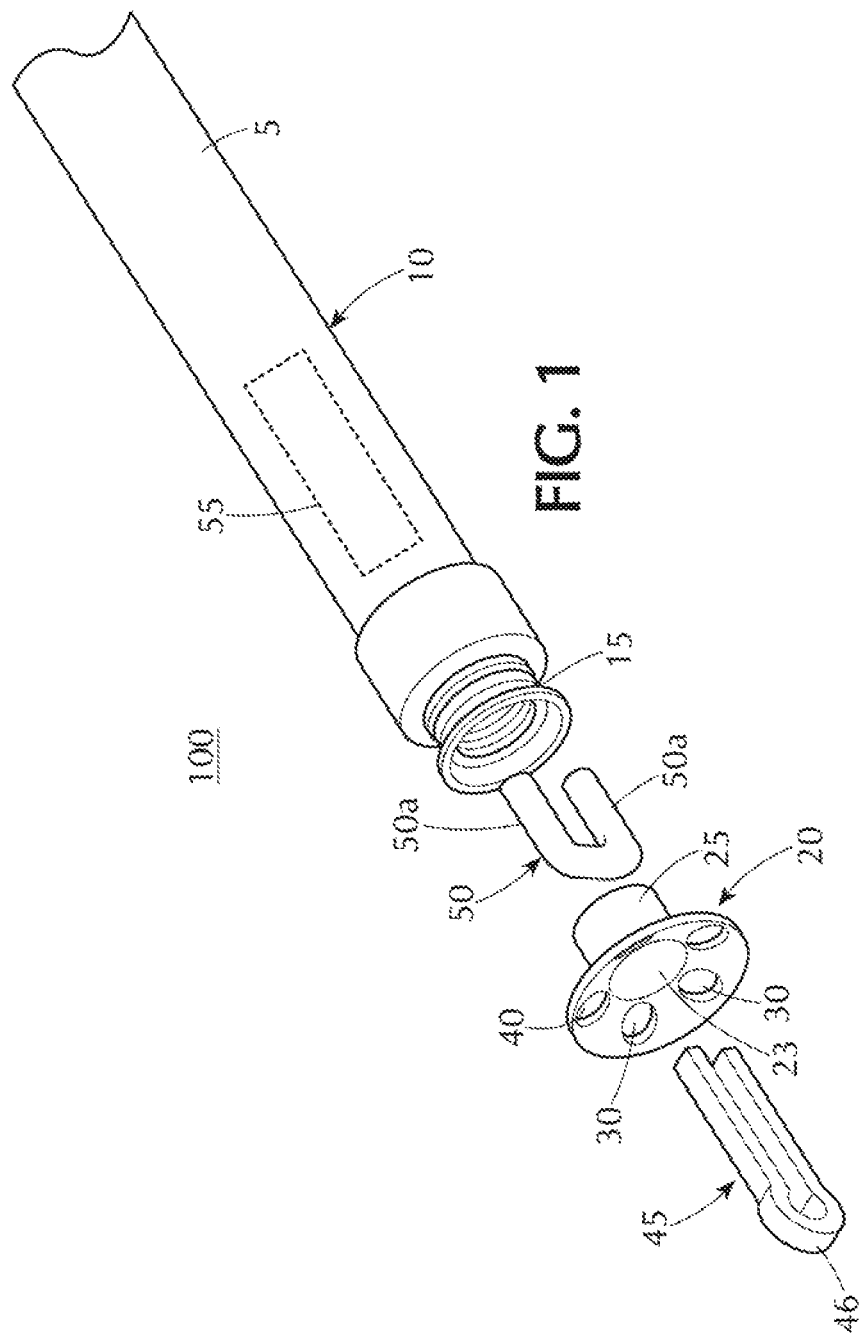
FIG. 1 is an exploded view of an exemplary implantable vaso-occluding device delivery system with a non-planar heat chamber detachment mechanism in accordance with the present invention.
Figure 2:
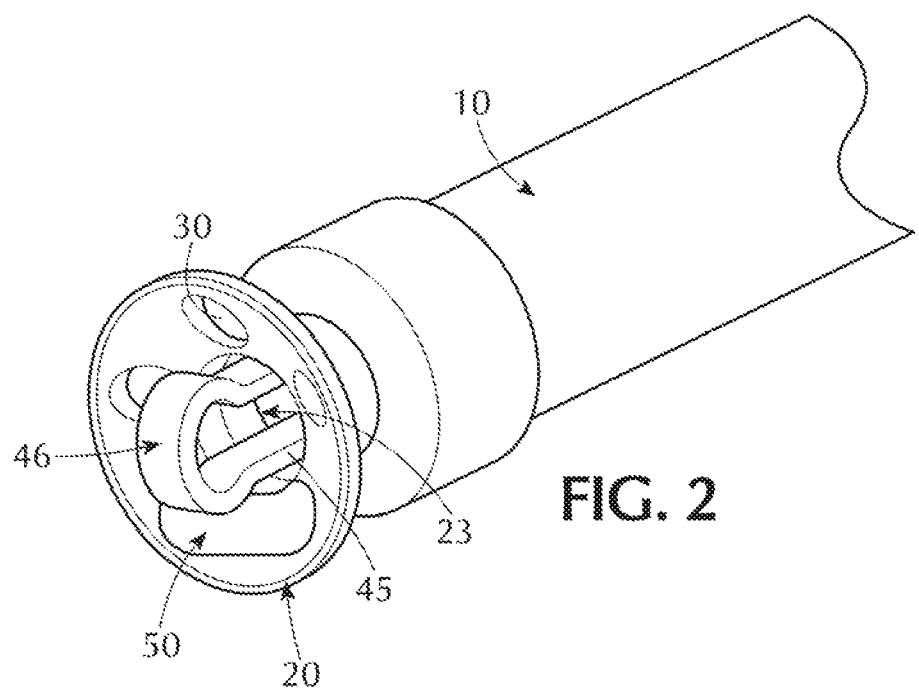
FIG. 2 is an oblique view of the delivery system of FIG. 1.
Figure 3:
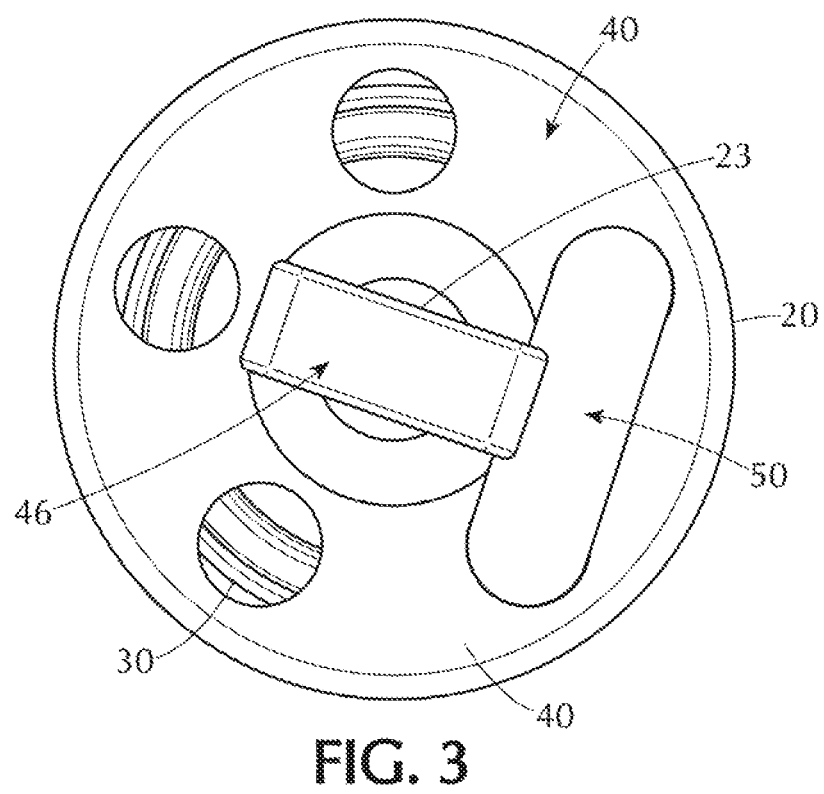
FIG. 3 is an end view of the delivery system of FIG. 2 when viewed from the distal end.
Figure 4:
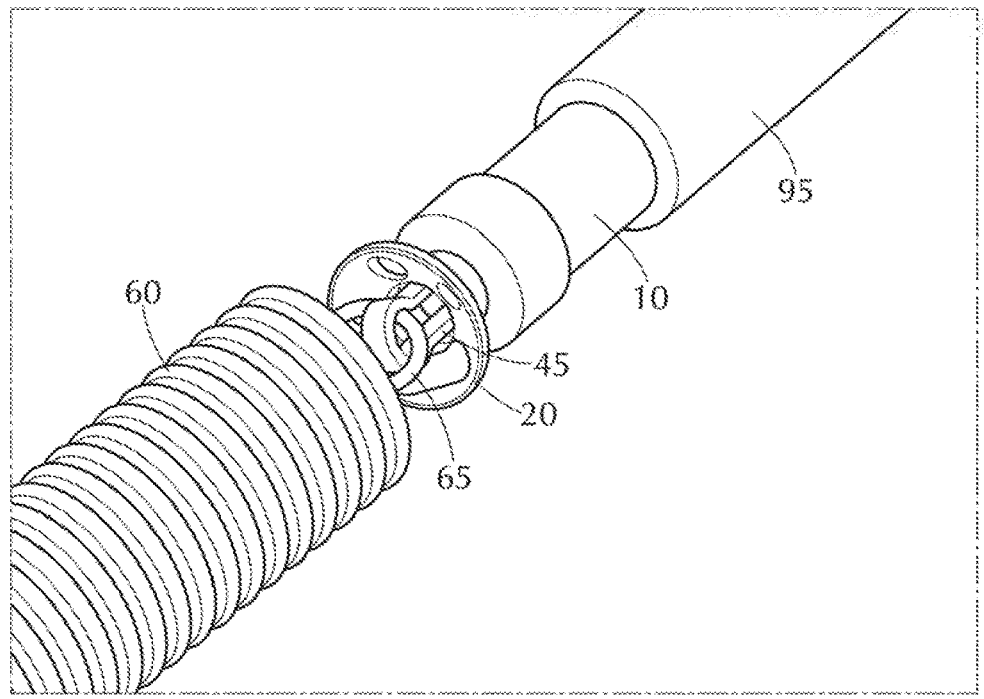
FIG. 4 depicts the delivery system of FIG. 1 with an exemplary embolic coil attached thereto.

FIG. 1 is an exploded view of an implantable vaso-occluding device delivery system with a non-planar heat chamber detachment mechanism in accordance with the present invention. Delivery system 100 includes an advancing member or pusher 10 having a proximal end 5 and a distal end 15. By way of illustrative example, the delivery system 100 illustrated in the figures and described herein is a catheter-based delivery system. An implantable vaso-occluding device 60, such as an embolic coil is attached to the distal end 15 of advancing member 10 via a polymer detachment fiber 45. It is to be noted, that the present inventive delivery system is not limited to that of an embolic coil and may be used with other implantable vaso-occluding devices.

Advancing member 10 is of sufficiently small diameter to fit within the lumen of the delivery catheter and preferably having sufficient columnar strength to transmit axial force distally while simultaneously be sufficiently flexible to navigate tortuous anatomies. The advancing member 10 may, but need not have, one or more of the following attributes: a hollow passageway; be electrically conductive; comprise composite layers or non-homogeneous material properties. Proximate the distal end 15 of the advancing member 10 is a non-planar heating chamber, bowl or dish 20. By way of illustrative example, the heating chamber 20 illustrated in the figures has a parabolic shape. Any non-planar shape is contemplated and within the scope of the present invention such as, but not limited to, elliptical or conical in shape. When viewed from the distal end 15 of the advancing member 10 the heating chamber 20 forms a concave, bowl or non-planar dish shape. An interior surface of the heating chamber 20 faces away from the distal end 15 of the advancing member 10, while its exterior surface faces the distal end 15 of the advancing member 10. Substantially centered and protruding from the exterior surface of the bowl or non-planar dish of the heating chamber 20 is a cylindrical tube or neck 25. Heating chamber 20 has a central opening 23 defined therein and extending longitudinally the entire length of neck 25 to form a passageway or channel therethrough. Extending radially outward from the central opening 23 of the heating chamber 20 is an enlarged non-planar collar 40. The outer diameter of the non-planar collar 40 is greater than the outer diameter of neck 25, while the outer diameter of the neck 25 is preferably sufficiently small to be received within an inner diameter of the distal end 15 of the advancing member 10. Neck 25 may be secured within the advancing member in any number of ways including, but not limited to the following: a press-fit; mechanically (e.g., via mating threads); or via adhesive.

One or more boles or openings 30 may be defined longitudinally through the non-planar collar 40 for introducing/threading/weaving one or more electrical heater elements/wires 50 longitudinally therethrough the advancing member 10 backwards towards its proximal end 5. In the exemplary embodiment illustrated in the figures, the non-planar collar 40 has five holes or openings 30, but this may be varied, as desired, to include any number of openings. Multiple openings 30 allow the number and arrangement of the heating wires or elements 50 on the heating chamber 20 to be adapted or reconfigured. Alternatively, the openings 30 may be eliminated altogether or reduced in number whereby the heating wires/elements 50 may be permanently attached to or embedded in the interior surface of the heating chamber 20. This is advantageous in that it allows for a greater number of heating elements without restriction of quantity of openings defined in the planar collar 40. Furthermore, eliminating or reducing the number of openings defined in the planar collar 40 provides a greater undisturbed surface area to focus heat.

The number of heating wires/elements 50 may be selected, as desired, with at least one or more heating wires/elements 50. Two electrical heating wires/elements 50 will generate heat at two different locations along the detachment fiber 45. Three electrical heating wires/elements 50 produce heat at three different locations along the detachment fiber 45, and so on. More than one heating wire/element 50 provides greater heat energy and/or the ability to provide heat energy at multiple locations at different times (e.g., for two detachment fibers 45). Furthermore, more than one heating wire/element 50 also advantageously insures reliable embolic coil separation or detachment at the target site. Greater heat energy may be retained by reducing the opening angle the angle subtended by two radii drawn from the midpoint of the central opening 23 to the outer edge of the non-planar collar 180° separation from one another) and/or depth (i.e., distance from the midpoint of the central opening 23 to an outer edge of the non-planar collar 40) of the non-planar heating chamber 20.

Referring to the exemplary embodiment shown in FIG. 1, the respective free ends 50a of a U-shaped heating wire/element 50 are received within two openings 30 (preferably two adjacent openings) defined longitudinally through the non-planar collar 40. Free ends 50a of the heating wire 50 preferably extend exterior of neck 25 through at least a portion, if not the complete longitudinal length, of the advancing member 10 towards its proximal end 5 and are electrically connected via electrical wires or leads to a power supply 55 providing electrical energy exciting the heating wire thereby producing heat. Preferably, the power supply is external to the human body; however, a battery (rechargeable or non-rechargeable) internal to the human body (e.g., disposed within the delivery system 100 itself) may alternatively be used. The type, location (external or internal to the human body), number of power supply may be varied, as desired, so long as energy is provided to excite the heating wire/element 50 thereby generating heat. Energy supplied to each of the heating wires/elements 50 may be substantially the same, or otherwise, may be varied, as desired, for each independent heating wire/element may be connected to respective different power supplies.

Advancing member 10 is secured to a vaso-occlusive device 60 (e.g., embolic coil) via a detachment fiber 45, preferably made of a polymeric material such as polyethylene, polypropylene or any other relatively thinly extrudable polymer that is able to be melted by heat. The exemplary detachment fiber 45 illustrated is a U-shaped fiber having an enlarged closed distal end 46 secured or linked to the embolic coil 60. For example, one of the free ends 45a of the detachment fiber 45 is threaded through a securing member 65 (e.g., ring) disposed on the proximal end of the embolic coil 60 and secured therein by the enlarged closed end 46. Free ends 45a of the detachment fiber 45 extend back through the opening 23 and advancing member 10 towards its proximal end 5, while the enlarged closed end 46 engages with thereby preventing its passage through the central opening 23. The detachment fiber 45 may be secured within the passageway/lumen of advancing member 10 by mechanical means, friction or adhesive.

Figure 5:
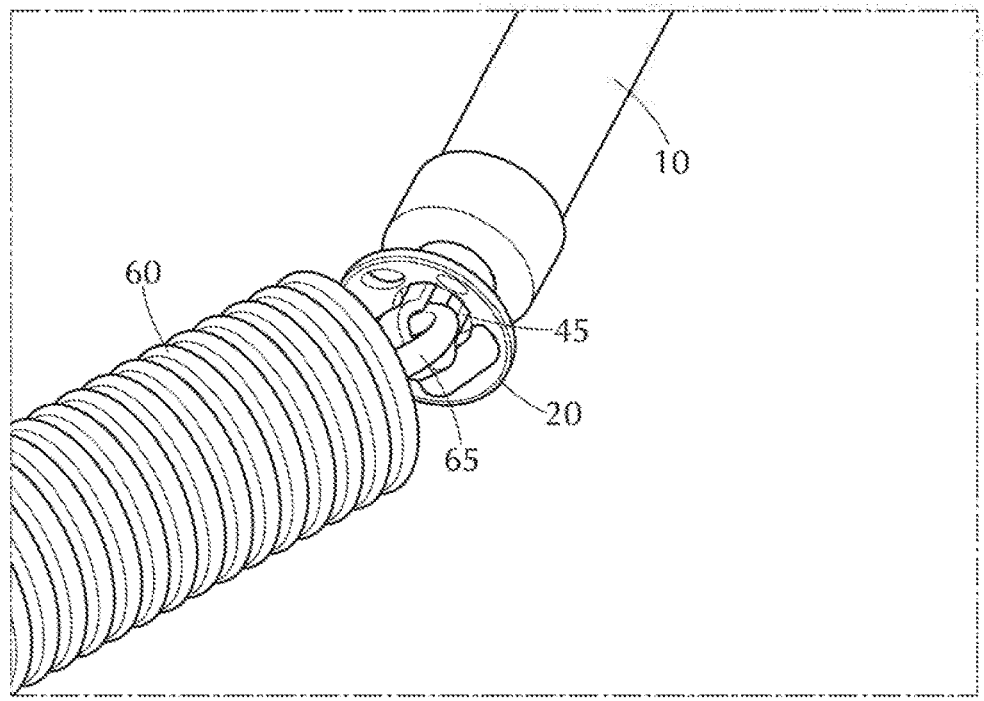
FIG. 5 shows the delivery system of FIG. 4 illustrating the articulation point and self-centering features of the present invention.

The non-planar shape of the hating chamber has numerous advantages, for instance: (i) providing an articulation point between the proximal end of the occluding device and the distal end of the delivery system (see FIG. 5), (ii) self-centering at all times of the occluding device is maintained while being delivered/advanced through the tortuous human anatomy; and (iii) maintaining physical contact at all times between the detachment fiber and heating elements/wires so as to minimize energy required to detach the occluding device from the delivery system.

The present invention detachment mechanism for an implantable vaso-occluding device delivery system is suitable for treatment of a diverse array of medical disorders throughout the body. However, due to difficulties associated with treating disorders of the brain, the present inventive detachment system is particularly beneficial due to the minimized expended energy required to melt/sever the detachment fiber that minimizes damage to surrounding brain tissue.

In operation, the vaso-occluding device 60 to (e.g., embolic coil) is assembled/installed on the advancing member 10. One of the free ends 45a of the detachment fiber 45 is passed through the securing member 65 (e.g., ring) disposed proximate the proximal end of the embolic coil 60. For instance, the detachment fiber 45 is threaded, looped, hooked or otherwise passes through the ring or other mechanical securing device 65 of the embolic coil 60 secured thereon by the enlarged closed end 46. The free ends 45a of the detachment fiber 45 are inserted into the opening 23 and through the advancing member 10 until its enlarged closed, end 46 rests in physical contact against without entering the opening 23. The advancing member 10 and embolic coil 60 secured thereto together are introduced into a delivery catheter 95. Once assembled, the delivery catheter 95 together with the advancing member and embolic coil is introduced into the body and traverses through the blood vessel to a target site. When the occluding device 60 reaches the target site within the body, the advancing member 10 is deployed to push the embolic coil 60 out from the delivery catheter 95 at the target site. The heating wire 50 is then energized by the power source 55 (either internal or external to the body) causing the detachment fiber 45 to melt or sever. The severed detachment fiber 45 allows the occluding device 60 to free itself from the advancing member 10 and remain positioned at the target site in the blood vessel. The delivery catheter 95 and advancing member 10 may then be withdrawn from the body while the embolic coil remains in place at the target site.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A delivery system for an implantable vaso-occluding device, comprising:
   an advancing member having a distal end and an opposite proximal end;
   a non-planar heating chamber disposed proximate to the distal end of the advancing member; the non-planar heating chamber having an interior surface facing away from the distal end of the advancing member and an opposite exterior surface facing the distal end of the advancing member;
   a detachment fiber made from a polymeric material and having a closed distal end protruding from the interior surface of the non-planar heating chamber; and
   at least one heating element disposed on the interior surface of the non-planar heating chamber; the at least one heating element producing heat sufficient to sever the detachment fiber.

2. The delivery system in accordance with claim 1, wherein the non-planar heating chamber has a parabolic, elliptical or cone shape lateral cross-section.

3. The delivery system in accordance with claim 1, wherein the non-planar heating chamber has at least one opening defined longitudinally therethrough; the at least one heating element being threaded through the at least one opening.

4. The delivery system in accordance with claim 1, where in the non-planar heating chamber has a central opening defined therein.

5. The delivery system in accordance with claim 4, wherein the non-planar heating chamber has a neck projecting from the exterior surface;
   the neck having a channel longitudinally defined therein for receiving free ends of the detachment member fiber.

6. The delivery system in accordance with claim 4, wherein the closed distal end of the detachment fiber is enlarged to prevent a portion of the detachment fiber from passing through the central opening of the non-planar heating chamber.

7. The delivery system in accordance with claim 1, further comprising a power source electrically connected to the at least one heating element.

8. The delivery system in accordance with claim 1, wherein physical contact is maintained at all times between the detachment fiber and the at least one heating element.

9. A method for assembling a delivery system for an implantable vaso-occluding device; the delivery system including: an advancing member having a distal end and an opposite proximal end; a non-planar heating chamber disposed proximate to the distal end of the advancing member, the non-planar heating chamber having an interior surface facing away from the distal end of the advancing member and an opposite exterior surface facing the distal end of the advancing member; a detachment fiber made from a polymeric material and having a closed distal end protruding from the interior surface of the non-planar heating chamber; and at least one heating element disposed on the interior surface of the non-planar heating chamber; the at least one heating element producing heat sufficient to sever the detachment fiber; wherein the method comprises the steps of:

positioning on the interior surface of the non-planar heating chamber the at least one heating element;

securing the exterior surface of the non-planar heating chamber to the distal end of the advancing member;

threading one of two terminating free ends of the detachment fiber through a securing member disposed on the vaso-occluding device until the securing member physically contacts the closed distal end of the detachment fiber; and securing the two terminating free ends of the detachment fiber along with the vaso-occluding device to the distal end of the advancing member with the non-planar heating chamber disposed therebetween; the at least one heating element is disposed on the interior surface of the non-planar heating chamber to produce sufficient heat to sever the detachment fiber.

10. The method in accordance with claim 9, wherein a number and location of the at least one heating element is reconfigurable by threading the at least one heating element through at least one hole defined longitudinally through the non-planar heating chamber.

11. The method in accordance with claim 9, wherein an articulation point is established between a proximal end of the vaso-occluding device and a distal end of the delivery system.

12. A method for positioning an implantable vaso-occluding device at a target site within a blood vessel using a delivery system including: an advancing member having a distal end and an opposite proximal end; a non-planar heating chamber disposed proximate to the distal end of the advancing member, the non-planar heating chamber having an interior surface facing away from the distal end of the advancing member and an opposite exterior surface facing the distal end of the advancing member; a detachment fiber made from a polymeric material and having a closed distal end protruding from the interior surface of the non-planar heating chamber; and at least one heating element disposed on the interior surface of the non-planar heating chamber; the at least one heating element producing sufficient heat to sever the detachment fiber;c the method comprising the steps of:

introducing the delivery system into the blood vessel using a delivery catheter;

advancing the delivery catheter through the blood vessel to the target site;

deploying the advancing member to project the vaso-occluding device from the delivery catheter at the target site in the blood vessel;

energizing the at least one heating element from a power source to produce sufficient heat to sever the detachment fiber thereby freeing the vaso-occlusive device at the target site in the blood vessel; and extracting the delivery catheter and the advancing member disposed therein from the blood vessel while maintaining the vaso-occlusive device located at the target site in the blood vessel.

13. The method in accordance with claim 12, wherein an articulation point is established between a proximal end of the vaso-occluding device and a distal end of the delivery system.

14. The method in accordance with claim 12, wherein the vaso-occluding device remains at all times self-centered while being advanced.

\* \* \* \* \*